United States Patent [19]

Hood et al.

[11] Patent Number: 5,261,883
[45] Date of Patent: Nov. 16, 1993

[54] PORTABLE APPARATUS FOR CONTROLLING FLUID FLOW TO A SURGICAL SITE

[75] Inventors: Larry L. Hood, Lagnua Hills; Charles E. Beuchat, Irvine; Harold J. Walbrink, Laguna Niguel; Maurice M. Imonti, Dana Point; William T. Cleminshaw, Irvine, all of Calif.

[73] Assignee: Alcon Surgical, Inc., Fort Worth, Tex.

[21] Appl. No.: 991,083

[22] Filed: Dec. 14, 1992

Related U.S. Application Data

[63] Continuation of Ser. No. 603,373, Oct. 26, 1990, abandoned.

[51] Int. Cl.$^5$ ............................................. A61B 17/00
[52] U.S. Cl. ........................................ 604/153; 604/30; 606/107
[58] Field of Search ............... 604/22, 30, 31, 151–153, 604/247; 606/107; 128/DIG. 12

[56] References Cited

U.S. PATENT DOCUMENTS

| | | | |
|---|---|---|---|
| 2,812,716 | 11/1957 | Gray | 604/153 |
| 3,572,375 | 3/1971 | Rosenberg | 604/247 |
| 3,693,613 | 9/1972 | Kelman . | |
| 3,920,014 | 11/1975 | Banko . | |
| 4,030,495 | 6/1977 | Virag | 604/152 |
| 4,468,221 | 8/1984 | Mayfield | 128/DIG. 12 |
| 4,505,701 | 3/1985 | Navato | 128/DIG. 12 |
| 4,519,792 | 5/1985 | Dawe | 604/152 |
| 4,573,883 | 3/1986 | Noon et al. | 604/153 |
| 4,680,026 | 7/1987 | Weightman et al. | 604/902 |
| 4,705,500 | 11/1987 | Reimels et al. . | |
| 4,764,165 | 8/1988 | Reimels et al. . | |
| 4,804,364 | 2/1989 | Dieras et al. | 604/22 |
| 4,817,599 | 4/1989 | Drews . | |
| 4,832,685 | 5/1989 | Haines | 604/30 |
| 4,838,866 | 6/1989 | Marshall, Sr. | 604/152 |
| 4,908,015 | 3/1990 | Anis . | |
| 5,176,629 | 1/1993 | Kullas et al. | 604/153 |

FOREIGN PATENT DOCUMENTS

0356372 2/1990 European Pat. Off. .

OTHER PUBLICATIONS

Anis, Aziz Y., "Illustrated Step-by-Step Description of the Anis Dry Extra Capsular Cataract Extraction Technique with In-the-Bag Lens Implementation", *Seminars in Ophthalmology*, vol. 1, No. 2, Jun. 1986, pp. 113-129.

*Primary Examiner*—Ralph Lewis
*Attorney, Agent, or Firm*—James A. Arno; Jeffrey S. Schira; Christopher W. Brody

[57] ABSTRACT

A system and apparatus are disclosed for controlling amounts of fluid flow to and from a surgical site. The system includes a surgical handpiece having means including a passage for allowing fluid flow to and from a surgical site. A dispensing assembly is couplable to the handpiece for movement therewith and is selectively operable for automatically controlling continuously or discretely a controlled and metered amount of fluid flow to and from the surgical site.

7 Claims, 4 Drawing Sheets

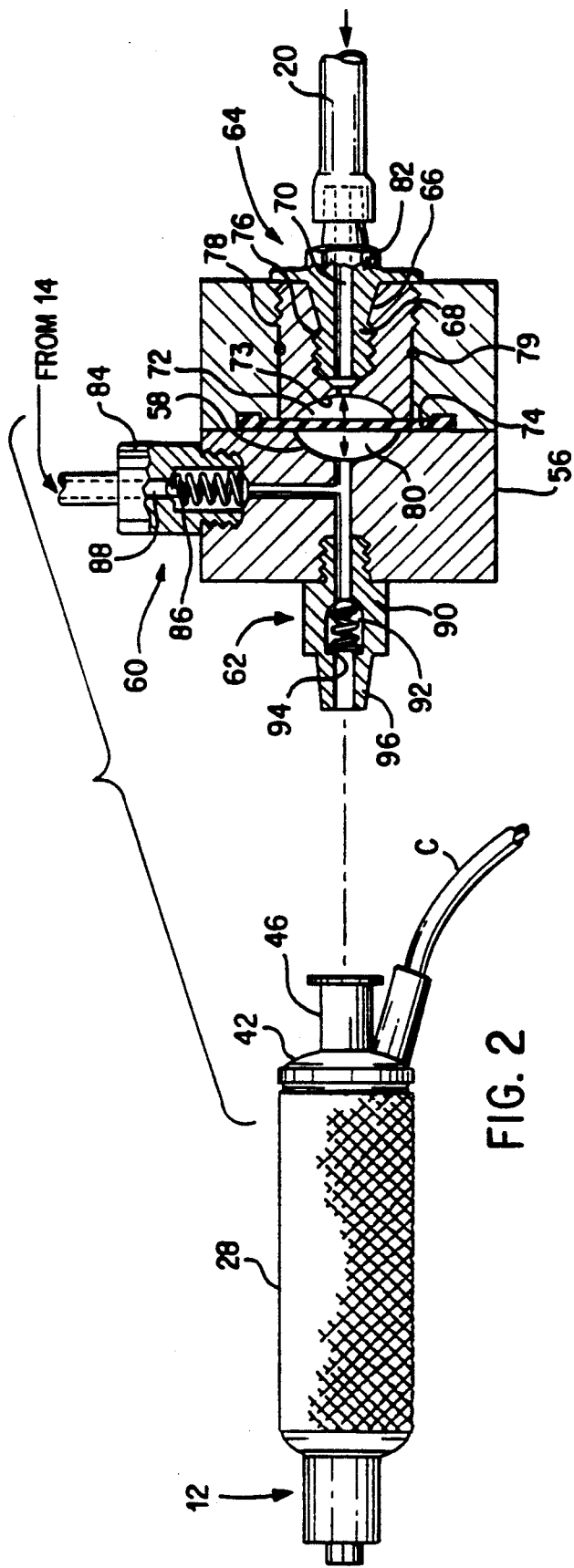
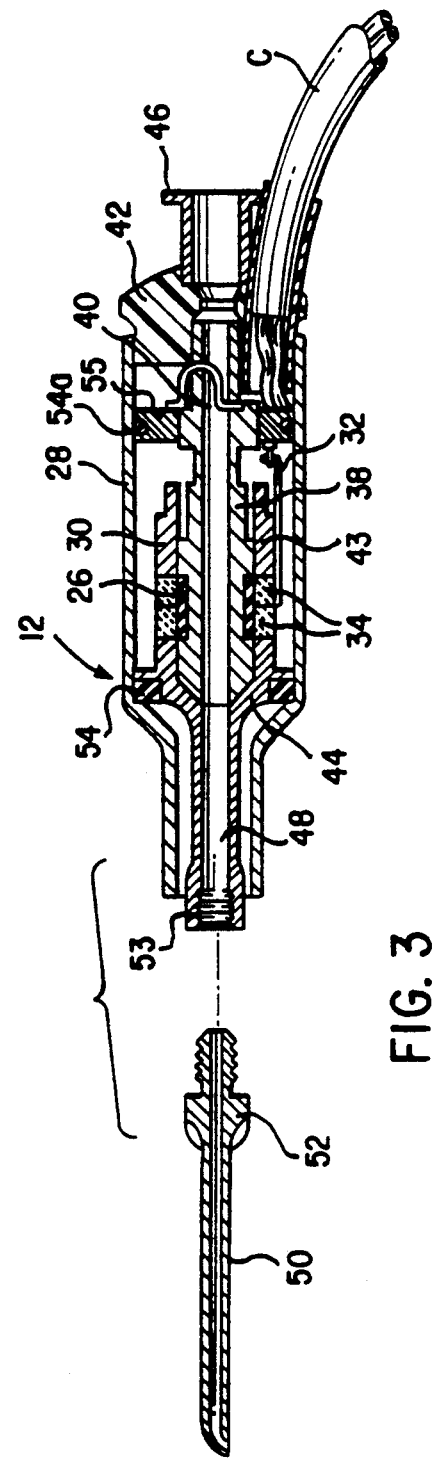
FIG. 2
FIG. 3

PORTABLE APPARATUS FOR CONTROLLING FLUID FLOW TO A SURGICAL SITE

This application is a continuation of Application Ser. No. 07/603,373 filed Oct. 26, 1990, now abandoned.

BACKGROUND OF THE INVENTION

This invention relates generally to a system and apparatus for controlling the flow of fluid to and from a surgical handpiece, and more particularly, to a handpiece used in ophthalmic surgery.

A number of techniques have been proposed for removing cataracts. One is described in an article by Aziz Y. Anis entitled, "Illustrated Step-by-Step Description of the Anis Dry Extra Capsular Cataract Extraction Technique with In-the-Bag Lens Implementation", Seminars in Ophthalmology, v. 1, N. 2, June 1986, pp. 113-129. Another technique is generally referred to as the phaco-emulsification technique disclosed in U.S. Pat. No. 3,693,613 to Kelman et al. In this latter approach, the cataract lens is fragmented and the fragmented lens tissue is aspirated. In both techniques, the anterior chamber of the eye is maintained at substantially the normal shape with a fluid. Moreover, it is desirable to control the amount of fluid dispensed by surgical instruments of the latter type It is common to control irrigating fluid to a surgical handpiece, such as used in ophthalmic surgery by a separate and relatively large control console that has a manually positionable switch movable to a plurality of positions or an automatic control loop/system. Another known kind of surgical handpiece is described in U.S. Pat. No. 4,764,165, in which part of the liquid dispensing apparatus is attached to the handpiece itself. In this apparatus a micro-motor controls dispensing of the fluid from the handpiece in response to operation of a foot-controlled mechanism.

Still another kind of technique and associated surgical handpiece for removing cataracts is described in U.S. Pat. No. 4,908,015, entitled, "Cataract Removal Technique", issued to Aziz Y. Anis. In this approach for removing cataraots, a hydrosonics handpiece instrument is utilized. In this latter handpiece, ultrasonic energy can be selectively applied to an operative probe extending from the handpiece housing. The probe when ultrasonically vibrated is used to mechanically penetrate the cataract lens. After or during ultrasonic energy application, however, treating fluid is metered into the eye through a fluid passage in the probe. Various kinds of medical treating fluids are supplied therethrough by a syringe being inserted into a passage which communicates with the probe passage. In this approach, small amounts of fluid, for example, between 1/500 and 1/100 a milliliter are used so as to separate the layers of the lens cortex and lens nucleus for achieving desired cataract removal. However, because a surgeon must control both the handpiece and a syringe when injecting the fluid, there is usually less than entirely satisfactory control of the instrument during the operative procedure.

SUMMARY OF THE INVENTION

In accordance with the present invention there is provided an improved system and apparatus which improve upon known approaches for controlling amounts of fluid to or from a surgical site.

Included is a system which comprises a surgical handpiece assembly having means including a passage for allowing fluid to be dispensed to or withdrawn from a surgical site; and, means couplable to the handpiece for movement therewith and being selectively operable for controlling the flow of fluid to or from the handpiece passage for displacing continuously or discretely a controlled and metered amount of the fluid to or from the surgical site.

In accordance with the present invention there is provided an improved system and apparatus which improve upon known approaches for delivering controlled amounts of fluid to a surgical handpiece Included is a system which comprises a surgical handpiece having means including a passage for allowing fluid to be dispensed to a surgical site; and, means directly couplable to the handpiece for movement therewith and being selectively operable for automatically controlling the supply of fluid to the handpiece passage for dispensing continuously or discretely a controlled and metered amount of the fluid to the surgical site.

In an illustrated embodiment, the controlling means includes a housing means defining a cavity and first and second passages leading into and from the cavity; respectively. Provision is made for displaceable means being displaceable within the cavity for defining an adjustable volume measurement chamber. Actuating means is provided which is operable for displacement within the cavity. The actuating means includes inlet and outlet valve means being respectively operatively associated with the first and second passages. The actuating means is operable for displacing the displaceable means so that a controlled volume of fluid, at a preselectable pressure, is introduced through the inlet valve means and into the measurement chamber. The actuating means is operable for displacing the displaceable means so that a controlled volume of fluid at the preselected pressure is dispensed from the chamber and the outlet valve means to the handpiece. Accordingly, a controlled and metered amount of fluid can be dispensed.

In another illustrated embodiment, there is provided an apparatus for use in a system for dispensing a controlled amount of fluid to a surgical handpiece having means including a passage for dispensing fluid to the surgical site. The apparatus includes means couplable to the handpiece and being selectively operable for automatically controlling the dispensing of fluid to the handpiece passage to the surgical site. The controlling means includes a housing defining a cavity and first and second passages leading into and from the cavity; respectively. There is provided displaceable means being displaceable within the cavity for defining an adjustable volume measurement chamber. There is provided means being operable for actuating said displaceable means for displacement within the cavity. There is provided inlet and outlet valve means being respectively operatively associated with the first and second passages. There is provided the actuating means being operable for displacing the displaceable means in a first direction so that a controlled volume of fluid at a preselected pressure is introduced through the inlet valve means and into the measurement chamber, and for reciprocating the displaceable means in a second direction so that a controlled volume of fluid, at a predetermined pressure, is dispensed from the chamber and the outlet valve means to the handpiece.

In still another illustrated embodiment, the controlling means includes an elongated housing defining the cavity, and the first and second passages respectively leading into and from the cavity are located on one end portion of the housing for orienting in an unobtrusive fashion the fluid lines connected to the controller.

The displaceable means is defined as piston means movable in the cavity to define the adjustable volume measurement chamber and the actuating means reciprocates the piston means.

In still another illustrated embodiment, the piston means is defined by a diaphragm mounted for movement within the valve body cavity.

In still another illustrated embodiment the actuating means is a pneumatic driver for pneumatically driving the diaphragm.

In still another illustrated embodiment, there is provided a variable volume adjustment device which controls the volume of the chamber.

In yet another illustrated embodiment, the controlling means includes both inlet and outlet devices, wherein each device is a check valve.

In still another illustrated embodiment, the piston means is defined by opposed dual area portions which multiply the forces applied one area portion.

In yet another illustrated embodiment, there is provided only a check valve at the inlet of the controlling means and predetermined hydraulic resistance at both the inlet and the outlet so as to control the volume therethrough.

In still another embodiment, there is provided an improved housing which includes a receiving portion for holding and protecting the handpiece.

Among the other objects and features of the present invention are the provision of an improved system and apparatus for controlling the amount of fluid to or from a surgical handpiece; the provision of an improved system and apparatus including an improved fluid controller which is couplable and movable with the handpiece; the provision of an improved system and apparatus for controlling the volume of fluid applied to or removed from a surgical handpiece; the provision of an improved system and apparatus for adjusting the volume supplied to a surgical handpiece; and, the provision of an improved system wherein the handpiece is a hydrosonics handpiece.

Still other objects and further scope of applicability of the present invention will become apparent from the detailed description to follow when taken in conjunction with the accompanying drawings in which like parts are designated by like reference numerals throughout the several views.

BRIEF DESCRIPTION OF THE DRAWINGS

FIG. 2 is a diagrammatic view illustrating some of the components thereof in cross-sectional view;

FIG. 3 is an elevational cross-sectional view of a surgical handpiece usable in this invention with the operative probe thereof removed;

DETAILED DESCRIPTION

Figure 1:
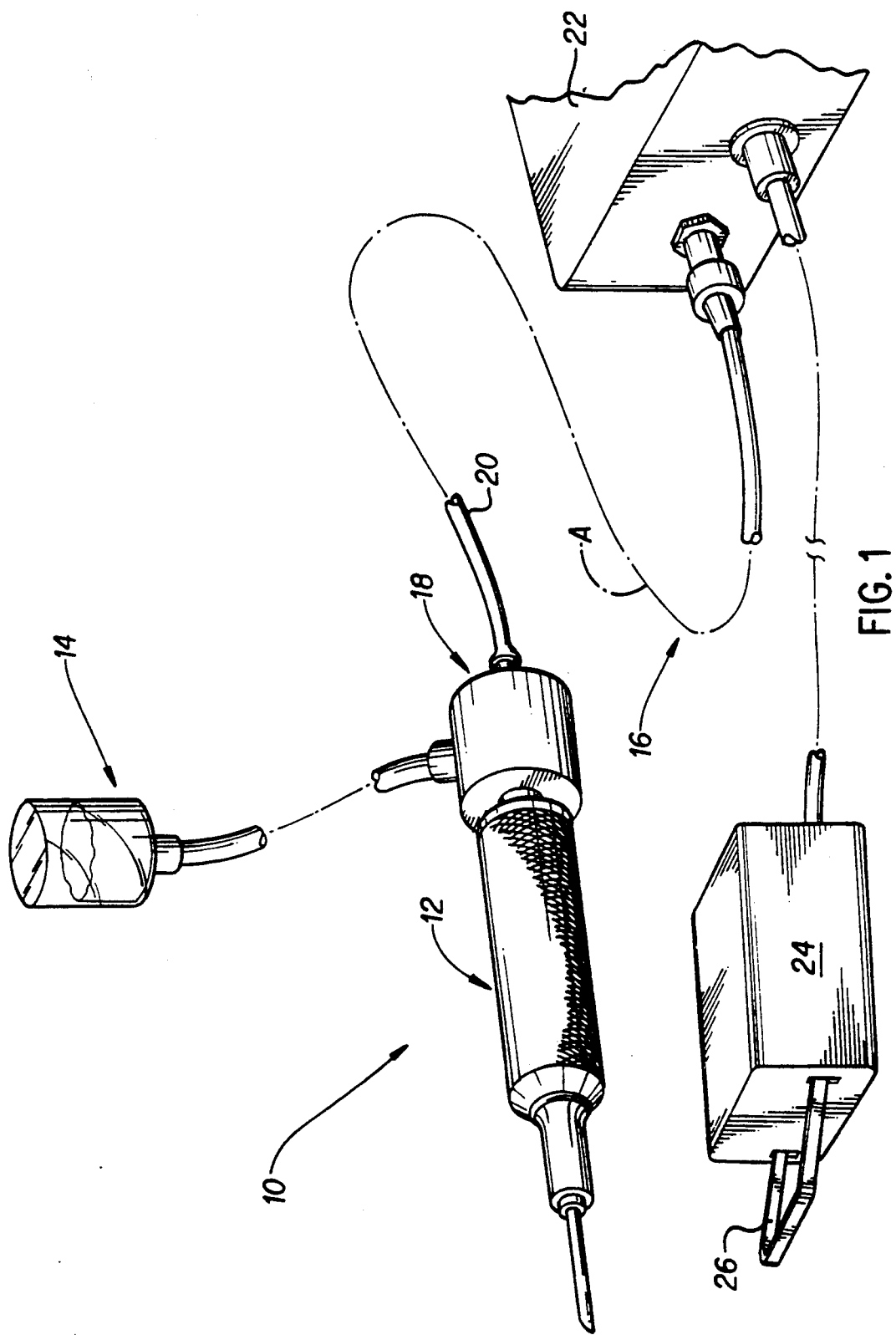
FIG. 1 represents a diagrammatic view of a system made in accordance with the present invention.

Reference is now made to the drawings for illustrating a fluid flow control system of the present invention represented generally by reference numeral 10. The system 10 includes a surgical handpiece assembly 12 which is made of a type similar to that described in U.S. Pat. No. 4,908,015. The handpiece assembly 12 has connected thereto, an external supply 14 of treating fluid which can be introduced into a human body. Treating fluids can include, but are not limited to, for example, BSS, enzyme and neutralizer fluids for use in cataract surgery, adhesives for wound closures and a variety of opthalmically acceptable pharmaceuticals. Other types of fluids are, of course, contemplated since this invention is not limited to ophthalmics.

The control apparatus 16 of this embodiment includes a portable dispensing apparatus 18 which is directly coupled to the handpiece assembly 12 and is operable to automatically dispense metered amounts of the fluid to the latter. As will be described, the controlled and metered dispensed fluid can be in continuous or discrete amounts. The term "continuous", as used in the specification and claims includes rapid pulses, for example, 1 cycle/sec. to 3 cycles/sec. By use of the terms discrete or measured volume as used in the specification and claims, it is meant that the pulses of fluid are not as rapid as continuous and can be applied over and for different periods of time. The dispenser apparatus 18 is fluidly connected by conduit 20 to a fluidic driver 22. A driver control means, such as a footswitch assembly 24 having a footswitch 26, or a switch integral to the handpiece 12 (not shown) is used to regulate the driver 22.

The invention contemplates that a wide variety of surgical handpieces can be used in conjunction with the control apparatus 16. However, reference is now made to the surgical handpiece assembly 12 which is shown in FIG. 3. In this embodiment, the handpiece assembly 12 includes a housing assembly 28 which retains therein an ultrasonic transducer assembly 30 which is selectively connected by a lead 32 from a cable C to a suitable control console (not shown) for driving a transducer assembly so as to generate ultrasonic vibrations. In this regard, the ultrasonic transducer assembly 30 is provided with a pair of generally annular shaped transducer washers 34, made of, for example, piezoceramic material. The transducer washers 34 are supported on an insulating sleeve 36 which is in turn supported on a reduced diameter portion of a central bolt member 38 having a fluid passageway 40 extending axially therethrough. An heel compression type nut 43 is provided so as to urge the washers 34 into firm engagement with an ultrasonic horn 44. The central bolt member 38 is joined at one end to a female locking luer fitting 46 which protrudes from the end cap 42 of the dispensing apparatus 18. The central bolt member 38 is threadedly connected to the ultrasonic horn 44, the latter of which has an axial passageway 48 fluidically communicating with the passageway 50 of a tubular surgical operative tip member 52. The operative tip 52 is threadedly connected to the ultrasonic horn 44 as at 53. The handpiece 12 includes an O-rings 54 and 54a and sealing wall 55. The foregoing described ultrasonic transducer assembly 30 defines means selectively operable for generating and transmitting ultrasonic vibrations to the operative tip 52 used in, for instance, cataract surgery to penetrate the lens. Other types of tips are contemplated for other kinds of tissue surgery, for coring or penetration of other tissues. In a cataract surgery, the tip 52 will penetrate the layers of the lens nucleus wherein the treating fluid is dispensed under pressure. In addition, small amounts of vibrational energy are applied to penetrate the lens. Fluid is injected into lens' layers so as to separate them. The lens fragments can then be removed by aspiration through a separate suction cannula (not shown).

Reference is now made to the dispensing apparatus 18, as shown in FIG. 2 for dispensing a metered amount of fluid to the surgical site. Included in the apparatus 18 is a valve body 56 having a valve cavity 58. An inlet passage means or assembly 60 is in fluid communication with cavity 58 and outlet means or assembly 62 is in fluid communication with the cavity 58. An axially adjustable vacuum inlet member 64 is threadedly disposed in an opening 66 of the valve body 56. The adjustable inlet member 64 comprises an elongated body 68 having a central passage 70 which is in fluid communication with a variable volume chamber 72 located on one side of a flexible diaphragm 74. The shape of the chamber 72 is important from the standpoint of insuring that the diaphragm 74 does not close-off the passage before conforming to the concave face 73 of the innermost portion of the inlet member 64. Additionally, the material of the diaphragm 74 should be selected so as to avoid exceeding stretch fatigue limits. Also, the diaphragm should have the resiliency and durometer to function as described. To avoid overstretching of the diaphragm, a suitable stop portion (not shown) can be provided. If desired, there can be provided a pair of diaphragms instead of a single one so as to provide a safety back-up should one rupture. The inlet member 64 is provided with an external threaded section 76 which threadedly cooperates with internal threads 78 formed adjacent the opening 66. An O-ring 79 is seated to provide a sealing engagement between the inlet member and the internal surfaces of the opening 66. As a consequence, the inlet member 64 can be axially moved relative to limit the stroke of the diaphragm 74. As will be appreciated this adjusts the size of a volume metering chamber 80 located to the left of the diaphragm 74 (as viewed in FIG. 2). For instance, the amount of fluid delivered can be between 1/500 and 1/100 of a milliliter. Other volumes are contemplated. The metering chamber 80 is in fluid communication with fluid inflow from the external supply 14 (FIG. 1) as well as in fluid communication with the outlet assembly 62 and to the surgical handpiece 12. The inlet member 64 further includes a threaded fitting 82 having the conduit 20 so that the 13 pressure fluctuation of the fluidic driver 22 can communicate with the chamber 72 as will be discussed subsequently.

Reference is now made to the inlet assembly 60 which includes an external inlet valve housing 84 a one-way check valve 86 in a passage 88 that is fluidly connected to the fluid supply 14 through suitable supply tubing. An external outlet valve housing 90 has a one-way valve 92 located in a passage 94. The outlet valve assembly 90 includes a male lock luer fitting 96 which is to be removably connected to the female fitting 46. The check valves 86 and 92 into and out of the metering chamber 80. Operation of both the inlet and outlet valve assemblies 60, 62 is done in response to actuation of the diaphragm 74 in response to operation of the driver 22. It will be readily appreciated that the check valve 92 should be much stiffer than check valve 86 because back pressure from the eye or other tissue might not allow proper seating at higher pulse rates. In addition, the check valve 86 should be able to withstand the various pressures of the supply fluid, such as when the supply bottle's height changes.

The fluidic driver 22 is of the type which does not, per se, perform an aspect of the present invention. Operation of such kinds of fluidic, pneumatic or hydraulic drivers are well known and one which is usable in conjunction with the present embodiment is commercially available from Alcon Surgical, Inc., of Fort Worth, Texas. Essentially the fluidic driver 22 effects rapid pulsations of positive and negative fluid pressure in the chamber 72. When vacuum is introduced into the chamber 72 the diaphragm 74 moves rightwardly and conforms to the internal shape of the cavity 58 as noted above. Accordingly, the inlet valve assembly 60 is operable to open so that the treating fluid fills the measuring chamber 80. Positive pressure against the diaphragm 74 expels fluid from the chamber 80 through the outlet valve assembly 62 and into the female fitting 46. Commencement and cessation of the pressure fluctuations are responsive to manipulation of the footswitch 24. This invention contemplates that the footswitch 24 can vary, through the driver 22, the pressure applied to the diaphragm and thereby the pressure of the fluid.

The present invention also contemplates that the diaphragm could be actuated, as noted above, by a rotary or reciprocating piston rod. Also, the diaphragm can be operated by a solenoid, or voice-coil type electromagnetically driven motor, electric motor or can be cable and threaded rod driven. A microprocessor that is suitably programmed can operate the diaphragm.

After the foregoing detailed description of the construction of the improved fluid handpiece assembly and system, the operations thereof are believed evident. Although a hydrosonics handpiece is used, a hypodermic surgical member can be used as well as other suitable assemblies.

Figure 4:
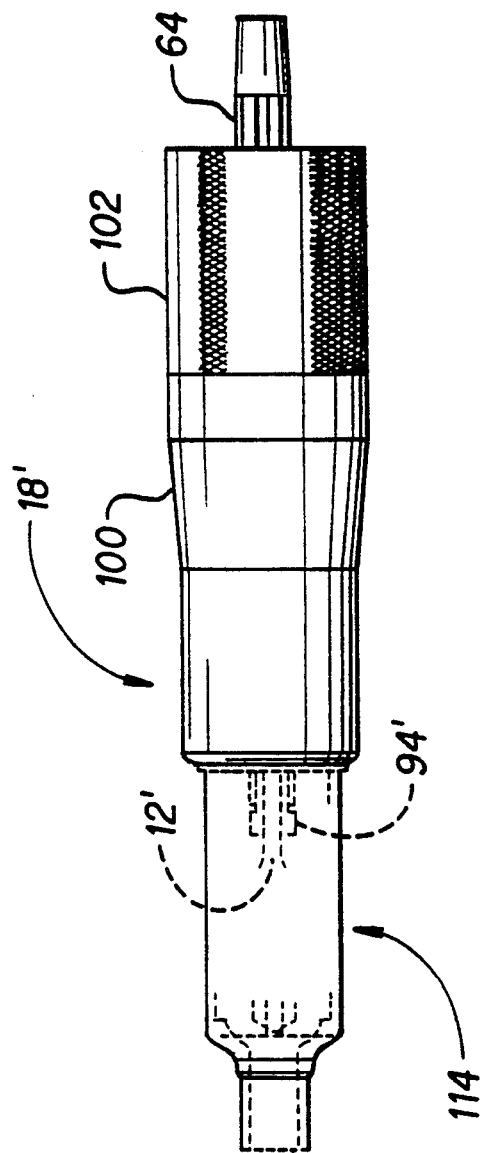
FIG. 4 is an elevational view of another preferred embodiment of the present invention.
Figure 5:
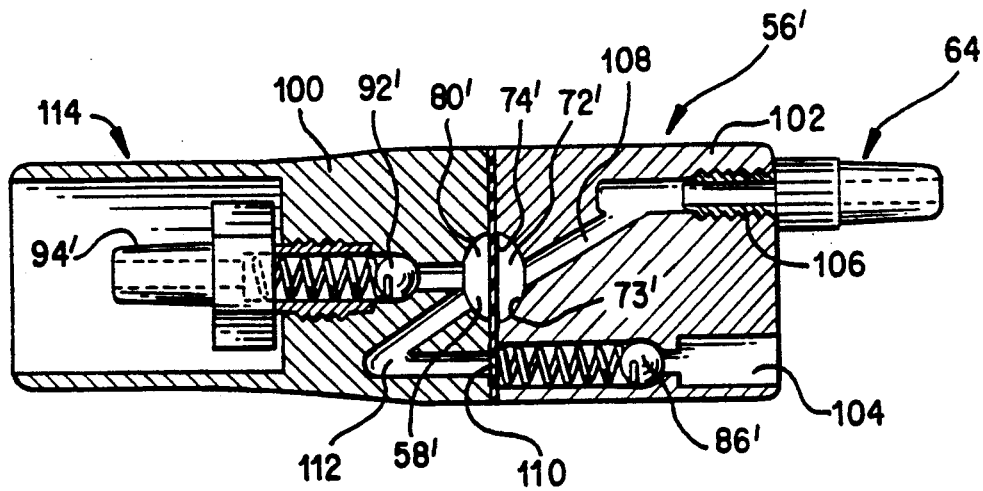
FIG. 5 is a cross-sectional view of the housing of the previous embodiment.

Reference is made to FIGS. 4 and 5 for illustrating another preferred embodiment of the present invention. In this particular embodiment, the dispensing apparatus is constructed so as to even more facilitate the portability aspect of the present invention, as well as minimize interference of the fluid lines connected thereto. The structure of this embodiment which corresponds to the structure of the previous embodiment will be designated by the same reference numeral with, however, the addition of a prime marking. The valve body 56' is defined by a generally elongated cylindrical body. The diaphragm 74' is adapted to reciprocate within the valve cavity 58'. In this particular embodiment, the valve body 56' is comprised of a first cylindrical housing section 100 and a second cylindrical housing section 102. In the first section 100 there is provided a female type locking luer opening 104 which fluidically communicates with an inlet check valve 86'. Diametrically opposed opening 104 is vacuum inlet member 64' that is threadedly disposed in an opening 106. The opening 106 communicates with a passage 108 leading into variable volume chamber 72'. The diaphragm 74' of this embodiment is like the previous embodiment. Also, the concave 73' of the second member 102 should be arranged so as to avoid the passage 108 closing-off prior to the diaphragm 74' conforming to the surface 73' of the housing section 102. The diaphragm 74' has an opening 110 which allows fluid communication between the fluid inlet 104 and the output chamber 80' by passage 112. The check valve 92' is in communication with the output chamber 80'. The check valve 92' is in fluid communication to a male locking luer 94'. The housing portion 100 includes a cylindrical barrel portion 114 which accommodates, with a sliding friction fit the exterior surface of the hydrosonics handpiece 12'. Other arrangements for releasably coupling are contemplated. This arrangement facilitates the ease by which an operator can utilize the hydrosonics handpiece and dispensing apparatus. It will be appreciated that while the hydrosonics handpiece 12' and the dispensing apparatus are couplable, the present invention envisions that the two components can be integrally formed into a single apparatus.

Figure 6:
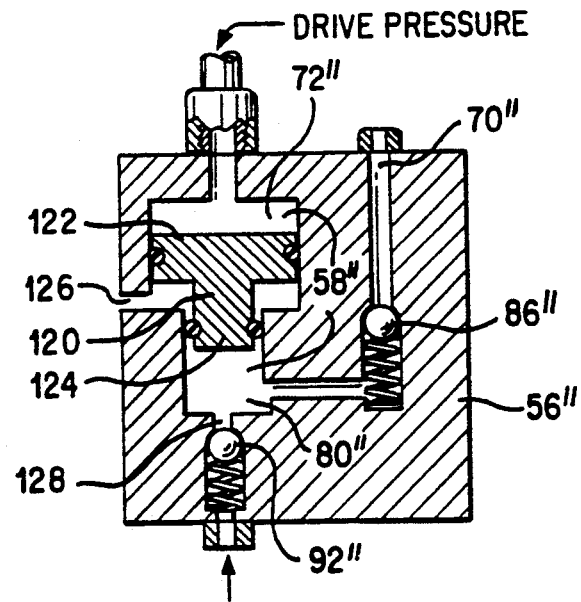
FIG. 6 is a schematic view of another preferred embodiment of the present invention.

Reference is now made to FIG. 6 for showing another preferred embodiment of this invention. In this particular embodiment, the same structure, as in the first embodiment, will be designated by like reference numerals with, however, the addition of a double prime (") marking. This embodiment differs from the previous insofar as the diaphragm 74 is replaced by a dual diameter piston assembly 120. The dual diameter piston assembly 120 is comprised of a relatively enlarged drive piston 122 which slidably moves in the chamber 72". The backside of the drive piston 122 is connected to a vent 126. Also, springs (not shown) could return the drive piston 122. The second or injection piston 124 is movable in a chamber 80". With the two relatively different diameters, as noted above, the ratio of their areas generates a force multiplication of the fluid drive pressure entering chamber 72" on the outlet pressure of fluid exiting the outlet valve 92". In other words, less driving pressure is required to force the fluid from the chamber 80. If the drive piston 122 is larger than the driven piston 124 the ratio is greater than 1. If the areas of the piston 120 and 122 are the same size the ratio is 1. Finally, if the injection piston 124 is larger than the drive piston 126 the ratio is less than one. This function in a manner like a hydraulic jack. Accordingly, with the foregoing less fluidic pressure need be introduced into the chamber 72" to effect the same output. Therefore, the driving force is multiplied by as a function of the ratio of the areas as noted.

Figure 7:
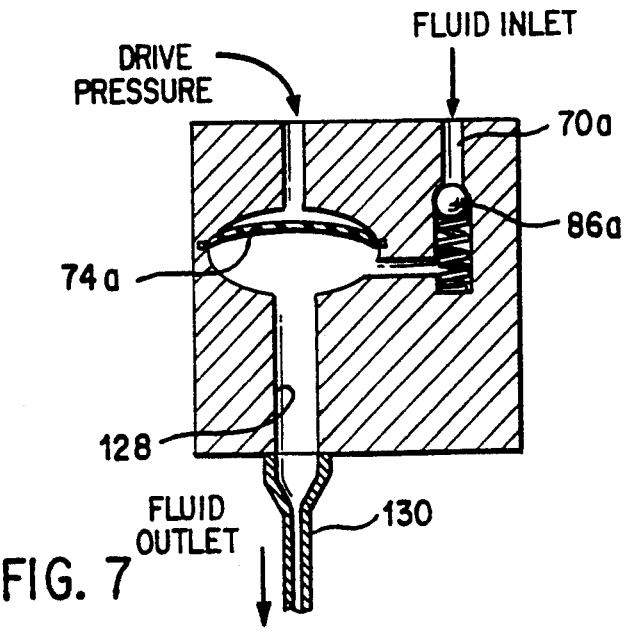
FIG. 7 is a schematic view of still another preferred embodiment of the present invention.

Reference is now made to FIG. 7 for showing another preferred embodiment of the present invention. Structure of this embodiment which is like that of the first embodiment will be indicated by like reference numerals with the addition of reference character "a". It will be noted that the valve body 56a is like the first embodiment except that the second check valve 92 on the outlet is not required. In this embodiment, when the diaphragm 74a is retracted, fluid will enter the inlet port through the check valve 86a and will travel through the outlet port from the chamber 80a. This is because there is no check valve. The fluid volume through each opening 70a and 128 will depend on the hydraulic resistance provided by each. If the outlet port 128 has a high hydraulic resistance relative to the opening 70a, such as when using 29 gauge needle 130, there will be sufficient fluid for injection through the latter. As is known, the 29 gauge needle 130 has a bore of approximately 0.007 inch. For example, the effective inlet diameter may be 0.070 inch. Thus, the ratio of hydraulic resistances of the noted inlets and outlets based on these areas will be 100 to 1, since area varies as a square of the diameter. Thus, the ratio of the inlet port to the outlet port, such as 29 gauge needle 130 is sufficiently large hydraulically that the second valve is not required and the desired flow is provided. The present invention envisions that the ratio of hydraulic resistance based on area be sufficient for purposes of providing the desired flow of fluid.

Reference is made now to the fact that the dispenser can be used as a suction pump to withdraw controlled amounts of fluid from the surgical site through the handpiece as opposed to dispensing fluid thereto. In this particular arrangement, for instance, the handpiece 12 would be fluidically connected to the valve housing 60 and a collecting device could be connected to the valve housing 62. Thus, operation of the diaphragm will cause fluid from the handpiece to enter the chamber 80.

Since certain changes may be made in the above-described system and apparatus without departing from the scope of the invention herein involved, it is intended that all matter contained in the description or shown in the accompanying drawings shall be interpreted as illustrative and not in a limiting sense.

What is claimed is:

1. A portable control apparatus for controlling fluid flow to a surgical handpiece comprising:
    a) a cylindrical housing having a first section and a second section;
    b) wherein said first section includes:
        i) a first recess in a proximal end face thereof;
        ii) an outlet check valve in communication with said first recess through an outlet passageway; and
        iii) an inlet passageway having one end in communication with said first recess and the other end terminating in an opening at the proximal end face and spaced apart from the first recess; and
        iv) means for coupling said first section and said outlet check valve to said surgical handpiece;
    c) wherein said second section includes:
        c) wherein said second section includes:
        i) a second recess in a distal end face thereof;
        ii) in inlet in communication with said second recess through a second passageway;
        iii) an inlet check valve having a first opening in the distal end face spaced apart from the second recess and in alignment with said opening of said inlet passageway and a second opening at a proximal end of said second section for connection to a source of fluid;
    d) a diaphragm disposed between said first and second sections, said diaphragm and said second recess forming an adjustable volume measurement chamber, said diaphragm and said first recess forming an outlet chamber interconnecting said outlet passageway and said inlet passageway, said diaphragm having a through hole aligned with said first opening of said inlet check valve and said opening at the proximal end face of said first section;
    e) wherein said inlet check valve, said outlet check valve and said inlet are aligned generally parallel to a longitudinal axis of said cylindrical housing; and
    f) wherein said inlet is connectable to a means for deflecting said diaphragm to adjust the volume of said adjustable volume measurement chamber and control dispensing of fluid from said fluid source successively through said inlet check valve, said through hole, said inlet passageway, said outlet chamber and said outlet check valve to said surgical handpiece.

2. The portable apparatus of claim 1 wherein said means for coupling comprises:

i) a hollow barrel section adapted to slidably receive a distal end of a surgical handpiece; and ii) a male type luer fitting mounted within said hollow barrel section for coupling to a port on the surgical handpiece.

3. The portable apparatus of claim 1 wherein said means for deflecting said diaphragm comprises a vacuum source.

4. The portable apparatus of claim 3 wherein said vacuum source comprises a fluid driver for causing said diaphragm to reciprocate.

5. The portable apparatus of claim 4 further comprising a footswitch for controlling said fluid driver.

6. The portable apparatus of claim 1 wherein said inlet and said inlet check valve are diametrically opposed on a proximal face of said second section.

7. The portable apparatus of claim 1 wherein each of said inlet and outlet check valves are spring biased.

* * * * *